United States Patent [19]

Pearlman

[11] Patent Number: 5,250,711
[45] Date of Patent: Oct. 5, 1993

[54] AMINE SALTS OF ALKANE-1,N-DICARBOXYLIC ACID MONO-(2-SULFATO-ETHYL) AMIDES

[75] Inventor: Bruce A. Pearlman, Kalamazoo, Mich.

[73] Assignee: The Upjohn Company, Kalamazoo, Mich.

[21] Appl. No.: 459,745

[22] PCT Filed: Jul. 1, 1988

[86] PCT No.: PCT/US88/02181
§ 371 Date: Jan. 12, 1990
§ 102(e) Date: Jan. 12, 1990

Related U.S. Application Data

[63] Continuation of Ser. No. 74,381, Jul. 16, 1987, abandoned.

[51] Int. Cl.$^5$ .............. C07D 75/00; C07D 7/00; C07D 213/18; C07C 309/15
[52] U.S. Cl. ..................... 552/575; 546/348; 562/105
[58] Field of Search .............. 552/575; 562/105; 546/348

[56] References Cited

U.S. PATENT DOCUMENTS 3,089,881  5/1963  Hershberg et al. ............... 552/575

FOREIGN PATENT DOCUMENTS 10056   5/1980  European Pat. Off. .
106453  4/1984  European Pat. Off. .
124233  1/1985  European Pat. Off. .
156642  10/1985 European Pat. Off. .

OTHER PUBLICATIONS

Jones Aldrichimica Acta. 9(3) 1976 pp. 35–45.

Primary Examiner—Mukund J. Shah
Assistant Examiner—E. C. Ward
Attorney, Agent, or Firm—Sidney B. Williams, Jr.

[57] ABSTRACT

Amine salts of alkane-1,n-dicarboxylic acid mono-(2-sulfatoethyl)amides of the Formula I $$HOC(O)-(CH_2)_n-C(O)-N(R_1)-CH_2CH_2SO_3^- {}^+HN(R_2)_3 \qquad I$$

wherein $R_1$ is selected from the group consisting of hydrogen, $C_1$–$C_8$ alkyl and phenyl, $R_2$ is $C_1$–$C_8$ alkyl or $(R_2)_3$ when taken together with the nitrogen atom is pyridinyl; and n is an integer from 4 to 20, their preparation and use to prepare water-soluble esters of corticosteroids.

8 Claims, No Drawings

AMINE SALTS OF ALKANE-1,N-DICARBOXYLIC ACID MONO-(2-SULFATO-ETHYL) AMIDES

This application is a continuation of U.S. application Ser. No. 074,381 filed Jul. 16, 1987, now abandoned.

BACKGROUND OF THE INVENTION

The present invention relates to amine salts of alkane-1,n-dicarboxylic acid mono-(2-sulfato-ethyl)amides I, their preparation and use as intermediates for the preparation of water-soluble esters of corticosteroids of Formula VII. Water-soluble esters of corticosteroids are known to be useful as injectable anti-inflammatory agents.

INFORMATION DISCLOSURE

Sulfonate containing prodrugs containing ester prodrugs of corticosteroids having the Formula VI, wherein St represents a corticosteroid moiety bonded to the carbonyl via the 21-hydroxy group of said corticosteroid are disclosed in U.S. Pat. No. 4,472,392. These compounds are also described by Anderson et al, *J. Pharm. Sci.* (1985), 74; pp. 365,375 and 382.

Corticosteroids such as methyl prednisolone can be converted into pharmaceutically useful water soluble derivatives by esterification with suberic acid-mono(2-sulfatoethyl-N-methyl)-amide monosodium salt ("suleptanic acid mono sodium salt"). Conventional processes for preparation of suleptanic acid involve treatment of suberic acid and N-methyl taurine with a coupling agent such as dicyclohexylcarbodiimide in a homogeneous, one-phase solution. Since, in a homogeneous solution, the two carboxylic acid groups of suberic acid have equal probability of reacting with N-methyl taurine, these processes afford statistically random mixtures of unreacted suberic acid, monoamide, and bisamide. Also, these conventional processes afford suleptanic acid in the monosodium salt form, which is hygroscopic. Thus, isolation in the anhydrous state required for esterification with the corticosteroid is quite laborious. Also, conventional processes for esterification of corticosteroids with the monosodium salt of suleptanic acid require very polar organic solvents such as dimethylformamide (DMF) because of the insolubility of suleptanic acid monosodium salt in less polar organic solvents. Separation of the desired corticosteroid suleptanate ester from the solvent DMF requires multiple extractions. Thus, conventional processes for preparation of suleptanate esters of corticosteroids are uneconomical.

SUMMARY OF THE INVENTION

The present invention provides:

A compound having the Formula I wherein $R_1$ is selected from the group consisting of hydrogen, $C_1$-$C_8$-alkyl and phenyl; $R_2$ is $C_1$-$C_8$ alkyl or $(R_2)_3$ when taken together with the nitrogen atom is pyridinyl; and n is an integer of from 4 to 20.

A compound having the Formula VI wherein $R_1$ is selected from the group consisting of hydrogen, $C_1$-$C_8$ alkyl and phenyl; $R_2$ is ethyl; n is an integer of from 4 to 20; and St is the residue of a corticosteroid and n is an integer of 4 to 20.

Also provided is a process for preparing the compounds of Formula I wherein $R_1$ is selected from the group consisting of hydrogen, $C_1$-$C_8$ alkyl and phenyl and $R_2$ is $C_1$-$C_8$ alkyl or $(R_2)_3$ when taken together with the nitrogen atom is pyridinyl which comprises (a) contacting a solution of the compound having the Formula II wherein R is selected from the group consisting of $C_1$-$C_8$ alkyl and phenyl, $C_1$-$C_8$ alkoxy, and substituted phenyl in a water-immiscible organic solvent with a water solution of the amine of the Formula III to prepare a compound of Formula IV; (b) treatment of an aqueous solution of the compound of Formula IV with a trialkylamine hydrohalide and hydrogen halide, and (c) recovery of the compound of Formula I from the reaction mixture formed in (b).

This process affords unexpectedly high yields of monoamides and unexpectedly low yields of bisamide. Condensation of n-methyl taurine with 1.25 molar equivalents of bis pivalic anhydride II by prior art, conventional processes is expected to afford a statistically random mixture of products (45% suberic acid, 60% monoamide, and 20% bisamide). However, the process described in this invention affords monoamide in 80.7% yield and bisamide in 4.7% yield (Example 1).

The invention further provides a process for utilizing the compound of Formula I to prepare novel compounds of Formula VI wherein $R_1$ is selected from the group consisting of hydrogen, $C_1$-$C_8$ alkyl and phenyl; $R_2$ is $C_1$-$C_8$ alkyl or $(R_2)_3$ when taken together with the nitrogen atom is pyridinyl and n is an integer of from 4 to 20 as well as water-soluble esters and salts of the corticosteroids of Formula VII; which comprises (a) treating a solution of the compound having the Formula I in a non-polar solvent, wherein $R_1$ is selected from the group consisting of hydrogen alkyl and phenyl; $R_2$ is $C_1$-$C_8$ alkyl or $(R_2)_3$ when taken together with the nitrogen atom is pyridinyl and n is an integer of from 4 to 20; with pivaloyl chloride and triethylamine followed by the compound having the Formula V and 4-dimethylaminopyridine to prepare a compound of Formula VI wherein St is the residue of a corticosteroid and (b) reacting the compound of Formula VI with a sodium salt. The use of the triethylammonium salt of methane-1,n-dicarboxylic acid mono-(2-sulfatoethyl)amide I allows the esterification reaction to be conducted in relatively cheap, low-boiling organic solvents such as methylene chloride, acetone and acetonitrile, which are easy to separate from the desired ester product.

The chemical formulas representing various compounds or molecular fragments in the specification and claims may contain variable substituents in addition to expressly defined structural features. These variable substituents are identified by a letter or a letter followed by a numerical subscript, for example, "$Z^1$" or "$R_i$" where "i" is an integer. These variable substituents are either monovalent or bivalent, that is, represent a group attached to the formula by one or two chemical bonds. For example, a group $Z_1$ would represent a bivalent variable if attached to the formula $CH_3-C(-Z_1)H$. Groups $R_i$ and $R_j$ would represent monovalent viable substituents if attached to the formula $CH_3-CH_2-C(-R_i)(R_j)H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parenthesis.

Chemical formulas or portions thereof drawn in a linear fashion represent atoms in a linear chain. The symbol "—" in general represents a bond between two atoms in the chain. Thus CH$_3$—O—CH$_2$—C(R$_i$)H-CH$_3$ represents a 2-substituted-1-methoxypropane compound. Carbonyl groups are represented by —C(O)—.

The term residue of a corticosteroid means the parent corticosteroid minus the 21-hydroxy group of said steroid which is necessary to form the novel esters of Formula V and the known esters of Formula VII. The parent corticosteroid is depicted as StOH wherein the OH is located at the 21-position as is described in U.S. Pat. No. 4,472,392. The term corticosteroid as used herein is taken to mean not only steroids produced by the adrenal cortex but also synthetic equivalents and is exemplified by the corticosteroids described in U.S. Pat. No. 4,472,392 and the pertinent-parts of said patents describing said corticosteroids are herein incorporated by reference.

The carbon atom content of various hydrocarbon-containing moieties is indicated by a prefix designating the minimum and maximum number of carbon atoms in the moiety, i.e., the prefix (C$_i$-C$_j$) indicates a moiety of the integer "i" to the integer "j" carbon atoms, inclusive. Thus (C$_1$-C$_8$)alkyl refers to alkyl of 1 to 8 carbon atoms, inclusive, or methyl, ethyl, propyl, butyl, and isomeric forms thereof.

As used herein the term substituted phenyl means phenyl substituted by one to 3, C$_1$-C$_8$ alkyl, halogen, C$_1$-C$_8$ alkoxy or nitro groups. Examples of substituted phenyl include 2,4,6-trichlorophenyl; 2,4,6-tribromophenyl; 2,6-dichlorophenyl, 2,6-dibromophenyl; 2,6-dinitrophenyl, 2,6-dimethoxyphenyl; 2,4,6-trimethylphenyl.

DESCRIPTION OF THE PREFERRED EMBODIMENT

The process for preparing the amine salts of alkane-1,n-dicarboxylic acid mono-(2-sulfatoethyl)amides of Formula I is illustrated schematically in Chart I. In step (a), a solution of the bis pivalic anhydride derivative of the symmetrical alkane-1,n-dicarboxylic acid of Formula II in a water-immiscible organic solvent such as methylene chloride, ethyl acetate or solvene is treated with a solution of the water soluble amine of Formula III in water in the presence of sodium bicarbonate and a tertiary amine to form a mono-amide of Formula IV. Dicarboxylic acids that can be used include suberic acid, sebacic acid, 1,10-decanedicarboxylic acid, 1,12-dodecanedicarboxylic acid and, and general any symmetrical alkane-1,n-dicarboxylic acid. The molar ratio of the bis-pivalic anhydride to water soluble amine is about 1:1 to about 2:1, optionally 1:15:1. The reaction is conducted at a temperature of about room temperature to about 80° C., preferably about 40° C. Reaction time is about 12 hours to about 48 hours. Any water-immiscible organic solvent can be used, including methylene chloride, and ethyl acetate solvene. The preferred solvent is methylene chloride.

In step (b), an aqueous solution of the monoamide of Formula IV is treated with a tertiary amine hydrohalide and hydrochloric acid to prepare the compound of Formula I. Tertiary amines can be used and include amines wherein the amine contains either C$_1$-C$_8$ straight or branch chain alkyl groups, i.e., trimethylamine, triethylamine, tri-n-propylamine, diisopropylethylamine, tri-n-butyl-amine and tri-n-octylamine. Other tertiary amines that can be used include pyridine, lutidine, collidine, quinoline and the like. The preferred tertiary amine hydrohalide is triethylamine hydrochloride. The molar ratio of the compound of Formula II to trialkyamine hydrohalide is about one to one, although a large excess of tertiary amine aminehydrohalide would not be harmful. The reaction is immediate at room temperature.

In step (c), the monoamide of Formula I is recovered from the reaction mixture by conventional processes such as extraction, evaporation, crystallization and combinations thereof. The preferred method of recovery involves extraction with tertiary butanol followed by vacuum evaporation.

The process for utilizing the compound of Formula I to prepare the water soluble esters of the corticosteroid of Formulas are illustrated schematically in Chart II.

In step (a), an amine salt of the alkane-1,n-dicarboxylic acid mon(2-sulfatoethyl)amide is dissolved in a non-polar solvent such as methylene chloride, acetone, or acetonitrile, then treated in succession with triethylamine, pivaloyl chloride, the corticosteroid of Formula V, and 4-dimethylamino-pyridine. The reaction is conducted at a temperature of about 0° C. to about 45° C., preferably about 25° C. for a period of about one hour to about 24 hours, usually about five hours. The use of the trialkylammonium salt allows the esterification reaction to be conducted in relatively cheap, low boiling organic solvents such as methylene chloride, acetone and acetonitrile, which are easy to separate from the desired watersoluble ester product. This represents an improvement over the use of the corresponding sodium salt, since the use of very polar solvents such as dimethylsulfoxide, dimethylformamide or pyridine is not required.

In step (b), an aqueous solution of the trialkylammonium salt of Formula VI is reacted with sodium hydrogen sulfate or other suitable sodium salt to provide the corresponding sodium salt of Formula VII. A large molar excess of the sodium salt is used (10 equivalents) although one molar equivalent may suffice. The sodium salt V can be recovered from the reaction mixture by conventional processes such as crystallization, evaporation, filtration, chromatography and combinations thereof.

Alkane-1,n-dicarboxylic Acid Mono-(-2-sulfatoethyl amides

Example 1

8-Oxo-8[(2-sulfatoethyl)methylamino]octanoic acid, disodium salt (Suleptanic Acid Disodium Salt)

A suspension of 1.707 g of suberic acid in 10.0 ml of methylene chloride was treated with 2.73 ml. of triethylamine, which produced a homogeneous solution. This solution was cooled to 0° C. then treated with a solution of 2.41 ml. of pivaloyl chloride in 2 ml methylene chloride. A white precipitate formed immediately; the slurry was stirred at room temperature for 30 minutes, then filtered under nitrogen pressure. The cake was washed with 5 ml. methylene chloride, and the combined filtrates added to an ice-cold solution of 1.660 g. N-methyltaurine sodium salt (76.1% aqueous slurry) and 0.823 g. sodium bicarbonate in 15 ml water. This reaction mixture was stirred at a rate such that the two phases were mixed but distinct at reflux for 65 hours. The aqueous layer, pH 5.64, was then acidified to pH 3.00 with 10% hydrochloric acid, and extracted with ethyl acetate (2×10 ml.). The aqueous layer (pH 3.35) was adjusted to pH 8.99 with 50% aqueous sodium hydroxide, then evaporated. The white residue was slurried in 40 ml isopropanol, and the solution evaporated under reduced pressure 6.323 mmoles, to yield 3.180 g. white powder, containing 2.1462 (80.7% yield from n-methyl taurine) of 8-oxo-8-[(2-sulfatoethyl)methylamino]octanoic acid, disodium salt (suleptanic acid) and 0.177% (0.372 mmoles, 4.7%) by bisamide LC.

Amine Salts of Alkane-1,n-dicarboxylic Acid Mono-(2-sulfatoethyl)amides

Example 2

8-Oxo-8-[(2-sulfatoethyl)methylamino]octanoic Acid, Triethylamine Salt (Suleptanic Acid, Triethylammonium Salt)

A crude suleptanic acid reaction mixture (208 ml; containing 29.895 g [94.20 mmoles] suleptanic acid and 2.9195 g [6.340 mmoles] bisamide by LC] was treated with triethylamine hydrochloride [12.969 g, 94.22 mmoles] and the pH lowered from 6.97 to 3.00 with concentrated hydrochloric acid. The resulting thin white slurry was then washed with ethyl acetate (3×110 ml). The aqueous layer was then treated with 18 g Na Cl, and the pH lowered from 3.27 to 2.03 with concentrated hydrochloric acid. This solution was then extracted with t-butanol (4×240 ml; the pH was readjusted from approximately 2.5 to 2.0 after each extraction). The extracts were then concentrated in vacuo to leave a white semi-solid residue, which was taken up in 100 ml acetone and stirred at room temperature for one hour. Some inorganic material (21.678 g) was then filtered off, and the filtrate concentrated in vacuo to leave a viscous oil (weight: 39.91 g) containing 34.595 g (87.24 mmoles, 92.6% recovery) 8-oxo-8-[(2-sulfoethy)methylamino]octanoic triethylamine salt (suleptanic acid triethyl-ammonium salt).

$^{13}$C-NMR (CD2C12); 175.74(S); 173.56(S); 49.89(t) and 48.92(t); 46.58(t); 46.35(t) and 44.78(t); 36.24(q) and 33.31(q); 34.22(t); 33.48(t) and 32.80(t); 29.08(t); 28.93(t); 25.01(t); 24.94(t); 8.75(g). The absorptions at 46.58 and 8.75 ppm reveal the presence of the triethylammonium cation.

Preparation of Water Soluble Esters of Corticosteroids

Example 3

Methylprednisolone Suleptanate Triethylammonium Salt

Triethylammonium suleptanate (2.34 g, 5.38 mmoles) in 10 ml methylene chloride was treated with triethylamine (1.10 g, 10.84 mmoles) ; the resulting colorless solution was treated dropwise with 603.8 mg trimethylacetyl chloride in 5 ml methylene chloride and the thin white slurry stirred at room temperature for 45 minutes. A suspension of methylprednisolone (1.01 g, 2.70 mmoles) in 10 ml methylene chloride was then added, followed by 26.1 mg (0.21 mmoles) dimethylaminopyridine; the resulting white slurry was stirred at room temperature for five hours, at which time conversion to methylprednisolone suleptanate, triethylamine salt was complete by LC.

Example 4

Methylprednisolone Sodium Suleptanate

The reaction mixture obtained in Example 3 was evaporated to a colorless oil, which was taken up in 20 ml of water. The resulting clear solution was treated with 3.59 g (26 mmoles) sodium hydrogen sulfate monohydrate and extracted three times with 20 ml portions of ethyl acetate. The aqueous layer was extracted three times with 20 ml sec-butanol and the combined sec-butanol extracts washed with two 30 ml portions of freshly-prepared 5% sodium bicarbonate-8% sodium sulfate, then with two 30 ml. portions of 10% aqueous sodium sulfate. The combined sec-butanol layers were evaporated and the residue taken up in 20 ml methanol. After evaporation at reduced pressure, the resulting white foam-was taken up in 3 ml methanol and filtered (the cake was washed with 2.0 ml methanol). The filtrates were evaporated and then dissolved in 2 ml methanol. The resulting pale yellow solution was added dropwise to 60 ml. ice-cold acetonitrile and the resulting white slurry stirred at 0° for 1.5 hr. The precipitate was filtered off, washed with 10 ml. ice-cold acetonitrile, and dried to yield 1.46 g (80.4%) methylprednisolone sodium suleptanate, as a free-flowing white powder (99% pure by LC analysis).

The compounds, 8-oxo-8-[(2-sulfoethyl)methylamino]octanoic acid, triethylamine salt and methylprednisolone suleptanate triethylammonium salt, and processes for preparing them and methods of using them to prepare the water soluble esters and salts of the methylprednisolone represent the best mode of carrying out the invention known at present.

FORMULAS

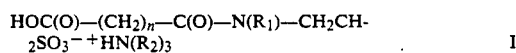

$$HOC(O)-(CH_2)_n-C(O)-N(R_1)-CH_2CH_2SO_3^- {}^+HN(R_2)_3 \qquad I$$

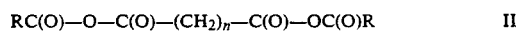

$$RC(O)-O-C(O)-(CH_2)_n-C(O)-OC(O)R \qquad II$$

$$R_1N(H)-CH_2CH_2SO_3Na \qquad III$$

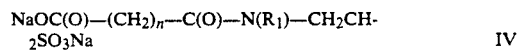

$$NaOC(O)-(CH_2)_n-C(O)-N(R_1)-CH_2CH_2SO_3Na \qquad IV$$

$$StOH \qquad V$$

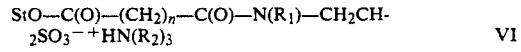

$$StO-C(O)-(CH_2)_n-C(O)-N(R_1)-CH_2CH_2SO_3^- {}^+HN(R_2)_3 \qquad VI$$

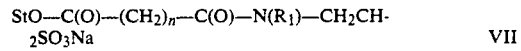

$$StO-C(O)-(CH_2)_n-C(O)-N(R_1)-CH_2CH_2SO_3Na \qquad VII$$

CHART I

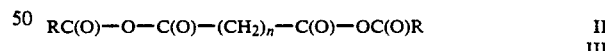

$$RC(O)-O-C(O)-(CH_2)_n-C(O)-OC(O)R \qquad II$$

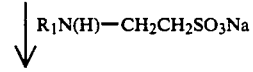

$$R_1N(H)-CH_2CH_2SO_3Na \qquad III$$

$$NaOC(O)-(CH_2)_n-C(O)-N(R_1)-CH_2CH_2SO_3Na \qquad IV$$

$$HOC(O)-(CH_2)_n-C(O)-N(R_1)-CH_2CH_2SO_3^- {}^+HN(R_2)_3 \qquad I$$

CHART II

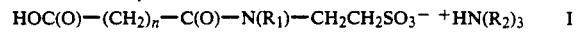

$$HOC(O)-(CH_2)_n-C(O)-N(R_1)-CH_2CH_2SO_3^- {}^+HN(R_2)_3 \qquad I$$

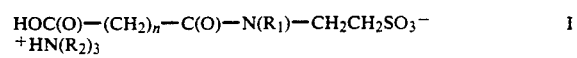

$$StOH \qquad V$$

-continued
CHART II

StO—C(O)—(CH$_2$)$_n$—C(O)—N(R$_1$)—CH$_2$CH$_2$SO$_3$$^-$ $^+$HN(R$_2$)$_3$   VI

↓

StO—C(O)—(CH$_2$)$_n$—C(O)—N(R$_1$)—CH$_2$CH$_2$SO$_3$Na   VII

I claim:

1. A compound having the Formula I

HOC(O)—(CH$_2$)$_n$—C(O)—N(R$_1$)—CH$_2$CH$_2$SO$_3$$^-$ $^+$HN(R$_2$)$_3$   I wherein R$_1$ is selected from the group consisting of hydrogen, C$_1$-C$_8$ alkyl and phenyl; R$_2$ is C$_1$-C$_8$ alkyl or (R$_2$)$_3$ when taken together with the nitrogen atom is pyridinyl; and n is an integer of from 4 to 20.

2. A compound according to claim 1 wherein R$_2$ is C$_1$-C$_8$ alkyl and n is 4 to 8.

3. A compound according to claim 2 wherein R$_1$ is methyl, R$_2$ is ethyl and n is 6.

4. A process for the preparation of compound having the Formula I

HOC(O)—(CH$_2$)$_n$—C(O)—N(R$_1$)—CH$_2$CH$_2$SO$_3$$^-$ $^+$HN(R$_2$)$_3$   I wherein R$_1$ is selected from the group consisting of hydrogen, C$_1$-C$_8$ alkyl and phenyl and R$_2$ is C$_1$-C$_8$ alkyl or (R$_2$)$_3$ when taken together with the nitrogen atom is pyridinyl which comprises (a) contacting a solution of the compound having the Formula II RC(O)—O—C(O)—(CH$_2$)$_n$—C(O)—OC(O)R   II wherein R is selected from the group consisting of C$_1$-C$_8$ alkyl, C$_1$-C$_8$ alkoxy, and substituted phenyl in a water-immiscible organic solvent with a water solution of the amine of the Formula III R$_1$N(H)—CH$_2$CH$_2$SO$_3$Na   III to prepare a compound of Formula IV;

NaOC(O)—(CH$_2$)$_n$—C(O)—N(R$_1$)—CH$_2$CH$_2$SO$_3$Na   IV (b) treatment of an aqueous solution of the compound of Formula IV with a trialkylamine hydrohalide and hydrogen halide, and (c) recovery of the compound of Formula I from the reaction mixture formed in (b).

5. A process according to claim 4 wherein the recovery of the compound of Formula I comprises extraction of the mixture formed in step (b) with t-butanol and then evaporation of the extract.

6. A process according to claim 5 wherein the alkane-1-dicarboxylic acid is suleptanic acid and the water soluble amine is N-methyltaurine and the compound formed is suleptanic acid, monosodium salt.

7. A process for the preparation of a compound having the Formula VII

StO—C(O)—(CH$_2$)$_n$—C(O)—N(R$_1$)—CH$_2$CH$_2$SO$_3$Na   VII which comprises (a) treating a solution of the compound having the Formula I HOC(O)—(CH$_2$)$_n$—C(O)—N(R$_1$)—CH$_2$CH$_2$SO$_3$$^-$ $^+$HN(R$_2$)$_3$   I in a non-polar organic solvent wherein R$_1$ is selected from the group consisting of hydrogen C$_1$-C$_8$ alkyl and phenyl; R$_2$ is C$_1$-C$_8$ alkyl or (R$_2$)$_3$ taken together with the nitrogen atom is pyridinyl and n is an integer of from 4 to 20; with pivaloyl chloride and triethylamine followed by the compound having the Formula V StOH   V and 4-dimethylaminopyridine to prepare a compound of Formula VI StO—C(O)—(CH$_2$)$_n$—C(O)—N(R$_1$)—CH$_2$CH$_2$SO$_3$$^-$ $^+$HN(R$_2$)$_3$   VI wherein St is the residue of a corticosteroid and (b) reacting the compound of Formula VI with a sodium salt.

8. A process according to claim 7 wherein the compound of Formula VI is the suleptanic acid triethylammonium salt of methylprednisolone and the compound of Formula VII is suleptanic acid sodium salt of methylprednisolone.

* * * * *